United States Patent [19]

Parodi et al.

[11] Patent Number: 5,650,477
[45] Date of Patent: Jul. 22, 1997

[54] LIQUID REACTIVE THERMOSETTING COMPOSITIONS AND PROCESS FOR THEIR CROSS-LINKING

[75] Inventors: Fabrizio Parodi, Genova; Renata Gerbelli, Milan, both of Italy; Mark DeMeuse, Delaware, Pa.

[73] Assignee: Enichem S.p.A., Milan, Italy

[21] Appl. No.: 570,636

[22] Filed: Dec. 11, 1995

[30] Foreign Application Priority Data

Dec. 21, 1994 [IT] Italy ............... 002587-94/A

[51] Int. Cl.$^6$ .............. C08G 59/68; C08G 65/10
[52] U.S. Cl. .............. 528/93; 528/94; 528/111; 528/112; 528/114; 528/116; 528/117; 528/118; 528/119; 522/65; 522/67; 522/153; 522/170; 428/35.7; 428/357; 428/413
[58] Field of Search .............. 528/93, 94, 111, 528/112, 114, 116, 117, 118, 119; 522/65, 67, 153, 170; 428/413, 35.7, 357

[56] References Cited

U.S. PATENT DOCUMENTS

| | | | |
|---|---|---|---|
| 3,923,725 | 12/1975 | Kadotani et al. | 523/461 |
| 4,033,911 | 7/1977 | Sandner et al. | 528/76 |
| 4,293,681 | 10/1981 | Malik | 528/115 |
| 5,006,626 | 4/1991 | Hofer et al. | 528/94 |
| 5,019,639 | 5/1991 | Hofer et al. | 528/94 |
| 5,145,880 | 9/1992 | Parodi et al. | 521/115 |
| 5,237,032 | 8/1993 | DeMeuse et al. | 526/314 |
| 5,288,833 | 2/1994 | Parodi et al. | 528/49 |
| 5,314,983 | 5/1994 | DeMeuse et al. | 528/73 |
| 5,326,833 | 7/1994 | Parodi et al. | 525/528 |
| 5,489,664 | 2/1996 | Parodi et al. | 528/73 |

FOREIGN PATENT DOCUMENTS

| | | |
|---|---|---|
| 0655472 | 5/1995 | European Pat. Off. |
| 1384206 | 4/1965 | France . |

OTHER PUBLICATIONS

Database WPI, Derwent Publications, AN-77-00917Y, JP-A-51-132280, Nov. 18, 1976.

*Primary Examiner*—Melvyn I. Marquis
*Assistant Examiner*—Randy Gulakowski
*Attorney, Agent, or Firm*—Oblon, Spivak, McClelland, Maier & Neustadt, P.C.

[57] ABSTRACT

Liquid reactive thermosetting compositions comprising:

A) At least one polyepoxide or a mixture of one or more polyepoxides with at least one monoepoxide, of an aliphatic, cycloaliphatic or mixed nature;

B) at least one anhydride of a di- or polycarboxylic acid of an aliphatic, cycloaliphatic or mixed nature;

C) at least one catalyst capable of promoting the rapid polymerization of the mixture A+B under microwave irradiation and having general formula (I):

$$N\equiv C-CH_2-CH(Z)-(O)_r-Y^+NR_1R_2R_3 \; X^-.$$

16 Claims, No Drawings

LIQUID REACTIVE THERMOSETTING COMPOSITIONS AND PROCESS FOR THEIR CROSS-LINKING

The present invention relates to liquid reactive thermosetting compositions.

More specifically, the present invention relates to liquid reactive thermosetting compositions comprising aliphatic or cycloaliphatic epoxy resins, anhydrides of di- or polycarboxylic acids also aliphatic or cycloaliphatic, and corresponding polymerization catalysts. These compositions have a prolonged period of reaction latency also at high temperatures, but are capable of polymerizing rapidly even at low temperatures under the effect of electromagnetic radiation, and are converted into either hard or tough, solid cross-linked polymeric materials.

The present invention also relates to the polymerization processes of these reactive compositions by a non ionizing electromagnetic radiation in the frequency range of microwaves.

These compositions are destined for a variety of applications requiring a critical combination of easy processability (in particular a prolonged reaction latency and low viscosity), polymerization rapidity under mild conditions, excellent dielectric properties, good adhesion to both organic and inorganic substrates. In particular, these systems are suitable for the rapid production of manufactured products, semi-manufactured products or devices requiring good resistance to prolonged exposure to sun light and artificial ultraviolet radiations.

The liquid reactive compositions consisting of aliphatic or cycloaliphatic epoxy resins and anhydrides of di- or poly-carboxylic acids, also aliphatic or cycloaliphatic have been used for many years as versatile thermosetting materials for a vast range of applications, such as the molding of electrical components, such as insulators, connectors, switches, etc., as casting or dipping resins for the encapsulation of electrical and electronic devices, and also adhesives, seals, linings, coatings, etc., for applications in out-door environments, i.e. requiring prolonged exposure to sun light.

Characteristics and applications of the systems consisting of epoxy resins and anhydrides are described for example in the following publications:

"Handbook of Epoxy Resins", by H. Lee and K. Neville, McGraw-Hill, New York, 1967 (or relative anastatic reprinting in 1982);

"Epoxy Resins—Chemistry and Technology", second edition, by C. A. May, Marcel Dekker, New York, 1988.

In particular, the applications and advantages of these cycloaliphatic systems as materials for electrical insulators are described for example in the publication "Cycloaliphatische Giessharze fuer Freiluftisolatoren", by F. Ehrhard, in the journal "Kunststoffe", vol. 74, pages 99–103, 1984.

The industrial importance of these thermosetting materials lies in the particular combination of the performances they offer: easy processability (comprising a prolonged reaction latency or pot-life), excellent dielectric properties, good thermo-mechanical characteristics, chemical neutrality (for example, with respect to epoxy resins hardened with amines or dicyandiamide, or phenolic resins cross-linked with urotropine), as well as good adhesion to inorganic and most polymeric materials. The aliphatic and cycloaliphatic epoxy/anhydride systems combine these characteristics with inertia to ultraviolet radiations, typical for example of fluoropolymers, silicon rubbers, aliphatic polyurethane elastomers, etc.

In contrast with this, however, the use of epoxy/anhydride systems, also non-aliphatic or cycloaliphatic, is of limited convenience from the point of view of productivity of manufactured or semi-manufactured products. Their hardening is in fact extremely slow, or does not occur at all, even at relatively high temperatures (120°÷160° C.), unless suitable polymerization catalysts are introduced, of which a wide variety are used industrially, such as tertiary amines and phosphines, alkylimidazoles, complexes of boron trifluoride, quaternary ammonium and phosphonium halides, etc., as described in the publication "Catalysts for Epoxy Molding Compounds in Microelectronic Encapsulation", by W. C. Mih, in "American Chemical Society Symposium Series", vol. 242, pages 273–283, 1984. Even with the use of these catalysts, however, the hardening processes require prolonged times of thermal treatment, up to 24 hours and over at temperatures typically within the range of 80°÷160° C., as evidenced in the above publications and following patents: U.S. Pat. No. 4,333,900, European patent application 444.741, French patent 2.577,232, Japanese patent applications 87-34.917, 87-161.818 and 89-98.616.

These suitable catalysts can, on the other hand, reduce the chemical resistance (in particular hydrolytical) and/or have negative effects on the electric properties of the manufactured product.

Only very low concentrations of catalysts are therefore acceptable in industrial practice.

Solidification times of the order of tens of minutes with low concentrations of catalysts can be obtained by strong heating (well above 160° C.), but these high treatment temperatures are not advisable or are even forbidden as they cause the loss of volatile components (for example, most of the anhydrides, epoxy diluents, etc.) particularly in the early stages of the solidification process, with modification of the system composition, fumes emissions, bubbles formation, or even strong degradation of the aliphatic and cycloaliphatic epoxy resins themselves, characterized by a scarce intrinsic thermal resistance.

For these reasons, the epoxide/anhydride thermosetting compositions cannot generally be used in manufacturing technologies involving a rapid solidification step, such as "Resin Transfer Molding" and "Compression Molding", "Pultrusion", "Pulforming", etc.

It is known that irradiation with electromagnetic waves in the frequency range of microwaves constitutes a convenient method for the heat processing of a wide variety of materials (such as wood, ceramics, glass, rubbers, resins, etc.) by virtue of the high heating rates and homogeneity which can be obtained also in large objects, and the minimum heat dispersions and energy consumption. In particular, various applications of rapid heating methods with microwaves to polymers, thermosetting resins and related composites are also known, both in melting or softening of the materials and heat molding of manufactured or semi-manufactured products, and in chemical polymerization processes (resin hardening and post-hardening), as described in the publication "Microwave Processing of Polymers—An Overview", by D. A. Lewis, in the volume "Microwave Processing of Materials III", Materials Research Society Symposium Proceedings, vol. 269, Pittsburgh, Pa. 1992, pages 21–31.

It is also known that a wide variety of compounds having a high dielectric dissipation factor (i.e. strongly dipolar compounds such as water, halohydric acids, sulfones, nitriles, amides, sulfonamides, etc.) have a high microwave absorption capacity, and can therefore undergo rapid and strong heating when subjected to these energy fields.

Microwave treatments have been proposed to accelerate the polymerization of various thermosetting resins, such as resins consisting of aromatic isocyanates and epoxides, according to what is described in U.S. Pat. No. 5,314,983, or epoxy systems, only of the aromatic kind. These processes are efficient and advantageous in terms of polymerization rapidity with respect to the normal methods of thermal treatment only if the reactive compositions contain groups with a high polarity of the type mentioned above, such as the isocyanic group in isocyanate/epoxide resins and, as indicated in the publication "Comparison of Microwave and Thermal Cure of Epoxy Resins", by J. Wei, M. C. Hawley, J. D. Delong and M. T. DeMeuse, in the journal "Polymer Engineering and Science", vol. 33, pages 1132–1140, 1993, for the aromatic epoxy composition consisting of bisphenol A diglycidylether (DGEBA) and 4,4'-diaminodiphenylsulfone (DDS).

Epoxy compositions characterized by low dielectric dissipation factor values, as they do not have groups with high polarity, such as the epoxide/anhydride systems of the aliphatic or cycloaliphatic type to which the present invention relates, could be made much more sensitive to microwave irradiation by introducing suitable non-reactive additives with high polarity. The introduction of these additives is known on an industrial scale to induce or enhance the capacity of microwave absorption, and consequent heating, of materials which are transparent or slightly sensitive to this type of irradiation (see, for example, the addition of N,N-diethyl-p-toluenesulfonamide to polyolefins, nylons, phenolic resins, etc.). As is known, considerable quantities of various parts per cent of these additives are necessary to provide the materials with significant sensitivity to microwaves.

Another known method of providing or increasing sensitivity to microwave irradiation, applied to epoxy thermosetting compositions, is the introduction of high weight percentages (typically ranging from a minimum of 5 to 50% by weight) of electrically conductive mineral powders, such as carbon black and copper, aluminium and iron powders.

Examples of this method are described in Japanese patent application 92-361-020 and in the two publications:

"Crosslinking under Microwaves of Aluminium Powder-Epoxy Resin Composites", by Y. Baziard and A. Gourdenne, in the journal "European Polymer Journal", vol. 24, pages 881–888, 1988;

"Interactions between Carbon Black-Epoxy Resin Composites and Continuous Microwaves", by A. Bouazizi and A. Gourdenne, in the journal "European Polymer Journal", vol. 24, pages 889–893, 1988.

Chemical additives with high polarity and conductive mineral fillers cannot be used however in many cases, as for example:

a. metallic powders cause increases, even very strong, of the resin viscosity and density of the final material;

b. electrically conductive powders generally cause dramatic deterioration in the dielectric properties;

c. compounds with high polarity induce or may increase the water absorption and reduce the hydrolytic resistance of the materials, making them less suitable or completely insuitable especially for out-door applications;

d. many additives, of aromatic nature such as N,N-diethyl-p-toluenesulfonamide mentioned above, can make the materials sensitive to UV radiations.

The Applicant has now found the possibility of overcoming the above limits in the processability of thermosetting compositions based on epoxy resins and anhydrides of carboxylic acids, both of aliphatic or cycloaliphatic nature, by combining the use of well-defined polymerization catalysts and irradiation treatments with a non-ionizing electromagnetic radiation.

The object of the present invention is therefore to provide liquid thermosetting compositions having a prolonged pot-life even when maintained at or subjected to high temperatures, but capable of polymerizing and solidifying rapidly, even at moderate temperatures, when subjected to irradiation with a non-ionized electromagnetic radiation or to a combination of this radiation and a conventional thermal treatment.

A further object of the present invention is to provide liquid reactive compositions and a process for carrying out their rapid transformation into a hard or tough cross-linked polymeric material which is suitable for the rapid production of manufactured, semi-manufactured products or devices for applications requiring excellent dielectric properties, good adhesion to both organic and inorganic materials, excellent resistance to prolonged exposure to sun or ultraviolet light, to water and air.

The Applicant has found that these and other objects can be conveniently reached by using the reactive compositions described hereinafter and subjecting them to a non-ionizing electromagnetic radiation in the frequency range of microwaves, or to microwave irradiation combined with a conventional thermal treatment.

The present invention therefore relates to liquid reactive thermosetting compositions comprising:

A) at least one polyepoxide or a mixture of one or more polyepoxides with at least one monoepoxide, of aliphatic, cycloaliphatic or mixed nature;

B) at least one anhydride of a di- or polycarboxylic acid of aliphatic, cycloaliphatic or mixed nature;

C) at least one catalyst capable of promoting the rapid polymerization of the mixture A+B under irradiation with microwaves and having general formula (I):

$$N\equiv C-CH_2-CH(Z)-(O)_r-Y^+NR_1R_2R_3\ X^- \qquad (I)$$

wherein the substituents have the meaning defined below.

According to the present invention, the polymerization process of these compositions comprises the following basic steps:

(i) mixing of components "A", "B", "C" and, optionally, other known reactive compounds, additives or known auxiliaries;

(ii) placing or transit of the composition in a microwave heating device;

(iii) rapid polymerization and solidification of the composition by microwave irradiation;

(iv) removal of the polymerized composition from the microwave heating device.

Organic polyepoxides and monoepoxides which can be used as component "A" for the preparation of the compositions of the present invention are organic compounds of aliphatic, cycloaliphatic or mixed type, whose molecule contains one (in the case of monoepoxides) or more epoxy groups. In component "A", which can consist of a mixture of different polyepoxides or polyepoxides with one or more monoepoxides, the average number of epoxy groups per molecule is a decimal number greater than 1 and preferably between 1.5 and 4.0. Preferred polyepoxides or their mixtures for the purposes of the present invention are those containing on an average from 2 to 4 epoxy groups per molecule.

For the purposes of the present invention all aliphatic, cycloaliphatic and mixed polyepoxides and monoepoxides of the prior art can be used. A large number of these are cited, together with many of the methods used for their preparation, in the publications "Handbook of Epoxy Resins" by H. Lee and K. Neville and "Epoxy Resins—Chemistry and Technology" by C. A. May mentioned above, the contents of which should be herein considered as a reference.

Polyepoxides which can be used according to the present invention are those obtainable by the polyepoxidation, for example by hydrogen peroxide or peracids, of compounds containing 2 or more double bonds of the olefinic type. Di- and poly-epoxides of this kind comprise: 1,2,3,4-diepoxybutane, 1,2,5,6-diepoxyhexane, 1,2,7,8-diepoxyoctane, 1,2,5,6-diepoxycyclo-octane, dicyclopentadienedioxide, 1-glycidyl-3,4-epoxycyclohexane, vinylcyctohex-3-ene dioxide, bis(4-glycidylcy clohexyl)ether, bis(4-glycidylcyclohexyl)methane, 2,2-bis(4-glycidylcyclohexyl)propane, bis(2,3-epoxycyclopentyl)ether, 2-(3,4-epoxycyclohexyl-5,5-spiro-3',4'-epoxycyclohexane)-methadioxane, bis(3,4-epoxycyclohexyl)adipate, 3,4-epoxycyclohexylmethyl-3',4'-epoxycyclohexanoate, 1,2,5,6,9,10-triepoxycyclododecane.

Other suitable di- and poly-epoxides of this type are those obtainable by the epoxidation of esters of polyols with unsaturated carboxylic acids, such as vegetable oils and synthetic or semisynthetic unsaturated triglycerides, polymers and copolymers containing double bonds of an olefinic nature such as polybutadiene, polyisoprene, polychloroprene and their copolymers with other vinyl monomers, as well as unsaturated polyesters such as those deriving from the condensation of unsaturated bicarboxylic acids (such as fumaric, maleic, itaconic and tetrahydrophthalic acid) and/or unsaturated diols (for example butenediol) with saturated bicarboxylic acids (such as succinic, adipic and hexahydrophthalic acid) and/or saturated diols (such as ethylene and diethylene glycols), 1,4-butandiol, 1,4-dimethylolcyclohexane, hexanediols).

Other polyepoxides which can be used are glycidylethers of aliphatic, cycloaliphatic or mixed diols and polyols, such as 1,3- and 1,4-butanediol, diethyleneglycol, 1,6-hexanediol, 1,4-dimethylolcyclohexane, neopentylglycol, bis(4-hydroxycyclohexyl)methane (or "hydrogenated Bisphenol F"), 2,2-bis(4-hydroxycyclo hexyl)propane (or "hydrogenated Bisphenol A"), polypropyleneglycols, glycerol, 1,1,1-trimethylolethane, 1,1,1-trimethylolpropane, pentaerythritol and castor oil.

Other suitable polyepoxides comprise polyglycidylesters of di- and poly-carboxylic acids of aliphatic, cycloaliphatic or mixed nature, such as succinic acid, glutaric acid, adipic acid, suberic acid, azelaic acid, sebacic acid, linoleic acid dimer and trimer, hexahydrophthalic acid, methylhexahydrophthalic acid and 1,4-cyclohexanedioic acid, as well as polyglycidylesters of polycarboxylic acids obtained by the condensation of one mole of a diol or polyol also of aliphatic or cyclaliphatic nature (such as ethylene or diethylene glycols, 1,3- and 1,4-butanediol and hexanediols, glycerol, 1,1,1-trimethylolethane, 1,1,1-trimethylolpropane) with a number of moles of an aliphatic, cycloaliphatic or mixed dicarboxylic acid such as those listed above (or the corresponding anhydride or chloride) equal to the number of hydroxylic groups of said diol or polyol.

Finally, polyepoxides suitable for the purposes of the present invention are polyepoxides consisting of polymers deriving from monomers containing epoxy groups, such as glycidylacrylate, glycidylmethacrylate and allylglycidylether, and copolymers of these monomers with other vinyl monomers, such as vinylacetate, alkylacrylates and methacrylates.

According to the present invention, mixtures of one or more aliphatic, cycloaliphatic or mixed monoepoxides with polyepoxides of the types indicated above, can also be used as component "A". These monoepoxides can be selected from the range of monoglycidylethers of alcohols and monoglycidylesters of carboxylic, sulfonic, phosphonic and other acids. Examples of these monoepoxides are: propyl-glycidylether, isopropyl-glycidylether, butyl-glycidylether, hexyl-glycidylether, 2-ethylhexyl-glycidylether, allyl-glycidylether, glycidylbutyrate, glycidylacrylate, glycidylmethacrylate, glycidyl 2-ethylhexanoate, glycidyl-laurate, glycidyl-stearate, glycidyl-oleate.

Other monoepoxides which can be used according to the present invention comprise those obtainable by monoepoxidation of compounds containing one or more double bonds of the olefinic type. Monoepoxides of this kind are for example: 1-methoxy-2-methylpropylene oxide, 1,2-epoxy-5-hexene, 1,2-epoxyhexane, 1,2-epoxy-decane, 1,2-epoxydodecane, 1,2-epoxyhexadecane, 1,2-epoxycyclohexane, 1,2-epoxy-5-cyclo-octene, 1,2-epoxy-7-octene, 1,2-epoxycyclododecane, 1,2-epoxy-5,9-cyclododecadiene, limonene oxide, 2-carene and 3-carene oxides.

Other monoepoxides are those resulting from the monoepoxidation of: mono- or poly-unsaturated carboxylic acids such as oleic acid, linoleic acid, linolenic acid and the related derivatives such as esters or amides; mono- or poly-unsaturated alcohols, such as oleilic alcohol, linalol and the related derivatives such as ethers or esters.

As already mentioned, component "B" of the compositions of the present invention consists of an anhydride, or a mixture of different anhydrides, of di- or poly-carboxylic acids of aliphatic, cycloaliphatic or mixed nature.

Suitable anhydrides of bicarboxylic acids comprise succinic anhydride, maleic anhydride, itaconic and citraconic anhydrides, hexahydrophthalic and methylhexahydrophthalic anhydrides, tetrahydrophthalic, methyltetrahydrophthalic and butenyltetrahydrophthalic anhydrides, acylcitric anhydrides such as acetylcitric anhydride, alkenylsuccinic anhydrides such as dodecenylsuccinic anhydride, nadic, methylnadic and bisnadic anhydrides. The corresponding halogenated derivatives, in particular chlorinated and brominated, can also be used, such as for example 2,3-dichloromaleic anhydride and chlorendic anhydride.

Among the anhydrides of polycarboxylic acids which are suitable for the purposes of the present invention are 1,2,3,4-cyclobutanetetracarboxylic dianhydride and 1,2,4,5-cyclopentanetetracarboxylic dianhydride.

Other anhydrides which can be used comprise the esterification products of the non-adjacent carboxylic group of anhydrides of tricarboxylic acids, such as tricarballylic anhydride, aconitic anhydride, and the adducts between maleic anhydride and poly-unsaturated aliphatic monocarboxylic acids such as linoleic and linolenic acids. Products of this type are those obtainable for example by the condensation of one mole of an alcohol (such as methyl, ethylic, butyl alcohols and cyclohexanol) or a polyol having at least 2 hydroxylic groups (such as ethylene glycol, 1,3- and 1,4-butanediol, neopentylglycol, glycerol, 1,1,1-trimethylolethane and -propane, known poly-esterdiols, -estertriols, -etherdiols and -ethertriols) with the chlorides of the same anhydrides of tricarboxylic acids, in stoichiometric ratios.

Anhydrides which are suitable for the purposes of the present invention are also polyanhydrides of bicarboxylic acids, such as polysebacic anhydride, polysuberic and polyazelaic anhydride, as well as various copolymers of maleic anhydride (and other unsaturated anhydrides such as those mentioned above) with different aliphatic, cycloaliphatic or mixed vinyl comonomers, such as vinylethers (for example methylvinylether, ethylvinylether, butylvinylether), vinylcyclohexane, vinylacetate and others.

The catalyst "C" of the present invention is a compound, or a mixture of different compounds, having general formula (I)

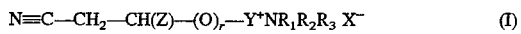

wherein
r can be 0 or 1;
Z can be hydrogen, or an aliphatic, cycloaliphatic, aromatic, heterocyclic or mixed radical, containing a number of carbon atoms of between 1 and 10;
$R_1$, $R_2$, $R_3$, the same or different, can be aliphatic, cycloaliphatic, aromatic, heterocyclic, or mixed radicals, jointly, $R_1$, $R_2$ and $R_3$ contain a number of carbon atoms of between 3 and 24. $R_1$ and $R_2$ can optionally form a heterocyclic, aliphatic or aromatic structure, comprising the quaternary nitrogen atom, as better expressed in the description of Y below;
Y can be an organic radical, containing a number of carbon atoms of between 1 and 16, having aliphatic, cycloaliphatic, aromatic, heterocyclic or mixed nature; Y can also be of a heterocyclic, mixed aliphatic-heterocyclic, mixed cycloaliphatic-heterocyclic nature, or also of the heterocyclic type with fused rings, comprising the quaternary nitrogen atom, and optionally also comprising other heteroatoms besides the quaternary nitrogen atom itself; when the quaternary nitrogen atom is part of a cycloaliphatic structure, this cycloaliphatic structure comprises one of the $R_1$ or $R_2$ radicals, or both; when the quaternary nitrogen atom is part of a heteroaromatic structure, or part of a cycloaliphatic structure with fused rings with the quaternary nitrogen atom belonging to two rings, this heteroaromatic or cycloaliphatic structure comprises both $R_1$ and $R_2$. $X^-$ is a halide anion selected from chloride, bromide, iodide, and, preferably, bromide and iodide.

According to the present invention this catalyst "C" can be prepared with any appropriate synthesis method known in organic chemistry. For the purposes of the present invention it is preferably prepared with two different methods depending on whether "r" in formula (I) is equal to 1, or equal to 0.

The catalyst "C" having formula (I) with "r" equal to 1 can be prepared preferably, but not exclusively, by a known cyanoalkylation process followed by the quaternization of the resulting tertiary amino-compound with an alkyl halide.

This process consists in the reaction of a hydroxyaminocompound, or a mixture of different hydroxyaminocompounds, having formula (II)

with a α,β-unsaturated nitrile, or a mixture of different α,β-unsaturated nitriles, having formula (III)

followed by the reaction of the tertiary amino-compound obtained, having formula (IV)

with an alkyl halide, or mixtures of different alkyl halides, having formula (V)

wherein Y, $R_1$ and $R_2$ in formula (II), Z in formula (III) and $R_3$ in formula (V) have the same meanings defined in the description of the catalyst having formula (I).

According to this synthesis method, the suitable hydroxyl-functional amino-compound having formula (II) is preferably selected from the groups of amino alcohols, alkanolaminoethers and aminophenols with a tertiary amino group, hydroxy-pyridines, hydroxyquinolines and hydroxyisoquinolines. Hydroxy-amino compounds of these types, which can be advantageously used, comprise: 2-dimethylaminoethanol, 2-diethylaminoethanol, 2-dibutylaminoethanol, 3-dimethylamino-1-propanol, 3-dimethylamino-2-propanol, 3-diethylamino-1-propanol, N-(2-hydroxyethyl)pyrrolidine, 1-ethyl-3-hydroxypyrrolidine, N-(2-hydroxyethyl)piperidine, 1-ethyl-3-hydroxypiperidine, N-(2-hydroxyethyl)morpholine, 2-(ethylphenylamino)ethanol, 2-[ethyl(3-methylphenyl)amino]ethanol, 4-dimethylaminophenol, 3-diethylaminophenol, 3-hydroxypyridine, 4-hydroxypyridine, 3-hydroxy-5-methylpyridine, 6-hydroxyquinoline, 5-hydroxyquinoline, 5-hydroxyisoquinoline.

The α,β-unsaturated nitrile of formula (III) is preferably selected from acrylonitrile, crotononitrile, 2-pentenenitrile, 2-hexenenitrile, 3-cyclohexylacrylonitrile and cinnamonitrile.

According to the above method for the preparation of the cyanoalkylamine of formula (IV), the hydroxyaminocompound (II) and the α,β-unsaturated nitrile (III) are reacted in such quantities that the molar ratio between the hydroxylic groups of compound (II) and the double olefinic bond of the nitrile (III) is not less than 1 and, preferably equal to 1.

The reaction can be carried out with the usual experimental procedures known to organic chemists for cyanoethylation and, in general, cyanoalkylation reactions.

In particular, the reaction between the tertiary hydroxyamino-compound (II) and the α,β-unsaturated nitrile (III) is conveniently carried out in the presence of a suitable catalyst consisting of a strong base preferably selected from: hydroxides of tetraalkyl-ammonium and -phosphonium, such as tetramethylammonium hydroxide, trimethylbenzylammonium hydroxide, tetrabutylphosphonium hydroxide and strong anion exchanger resins; hydroxides of alkali metals such as lithium, sodium and potassium hydroxides; alkoxides of alkali metals such as potassium methoxide and sodium ethoxide; hydrides of alkali metals such as lithium and sodium hydrides; amides of alkali metals such as sodium- and potassium-amide and lithiumdiethylamide, and mixtures thereof.

As already specified, the tertiary cyanoalkylamine having formula (IV) is reacted, in a second step, with an alkyl halide (V), to obtain the cyanoderivative of formula (I) containing a quaternary nitrogen atom which forms the polymerization catalyst "C" of the compositions of the present invention. The molar ratio between the alkyl halide and tertiary amino groups of the cyanoalkylamine must in this case be equal to, or greater than, 1 and preferably between 1.0 and 1.1. The reaction can be conveniently carried out according to the methods which are generally known in organic chemistry for the quaternization of tertiary amines.

R₃X halides which can be used in a particularly advantageous way according to the present invention are alkyl monoiodides and monobromides or their mixtures.

Preferred alkyl monoiodides comprise iodomethane, iodoethane, 1-iodopropane, 1-iodobutane, 1-iodopentane, 1-iodo-3-methylbutane, 1-iodohexane, 1-iodoheptane, 1-iodo-octane, 1-iododecane, 1-iodododecane, 1-iodohexadecane, 1-iodo-octadecane, allyliodide, benzyliodide, and their mixtures.

Suitable alkyl monobromides comprise bromomethane, bromoethane, 1-bromopropane, 1-bromobutane, 1-bromopentane, 1-bromo-3-methylbutane, 1-bromohexane, 1-bromoheptane, 1-bromo-octane, 1-bromodecane, 1-bromododecane, 1-bromotetradecane, 1-bromohexadecane, 1-bromo-octadecane, allylbromide, crotylbromide, benzylbromide, and their mixtures.

The above cyanoalkylation and quaternization reactions for the preparation of the catalyst "C" of the present invention can be carried out using the reagents and catalysts listed above alone, or in the presence of suitable solvents which are inert or not very reactive towards the functional groups present in the reaction mixture and, preferably, volatile enough to allow easy removal by distillation. Solvents which can be used for this purpose comprise tetrahydrofuran, dioxane, 1,2-dimethoxyethane, diisopropylether, terbutylmethyl-ether, hexane, heptane, cyclohexane, methylcyclohexane, benzene, toluene, nitromethane, and their mixtures.

The preparation of catalyst "C" is preferably carried out without solvents or in the presence of as small a quantity as possible thereof.

Typically, and for purely illustrative purposes which do not limit the scope of the present invention, a convenient process for the preparation of catalyst "C" comprises the following steps:

1.a. the α,β-unsaturated nitrile (or a mixture of different α,β-unsaturated nitriles) is gradually added, under stirring, to a liquid mixture consisting of the tertiary hydroxyamino-compound of formula (II) (or a mixture of these tertiary hydroxyamino-compounds), the catalyst consisting of one of the strong bases previously mentioned, and the possible solvent or mixture of solvents, maintained at a temperature within the range of 0° to 80° C.; this strong base being present in quantities of between 0.5 and 5 milliequivalents with respect to 100 g of the total mixture, comprising the α,β-unsaturated nitrile;

1.b. the reaction mixture obtained in (1.a) is maintained under stirring for a period of between 0.5 and 6 hours at temperatures of between 0° and 80° C.;

2.a. the alkyl monohalide is added to the mixture obtained in step (1.b), maintained under stirring at a temperature of between 0° and 40° C., and the stirring is then continued for a further period of between 0.5 and 6 hours in the same temperature range;

2.b. the mixture obtained in step (2.a) is heated, under stirring, to a temperature of between 50° and 120° C. and maintained at this temperature for a period of between 6 and 60 hours;

3. the possible solvent is removed from the mixture by evaporation at atmospheric pressure or, preferably, at reduced pressure, to obtain a residue consisting of polymerization catalyst "C".

Examples of catalysts which can be thus synthesized, as liquids at room temperature and useable with particular advantages in the compositions of the present invention are listed below:

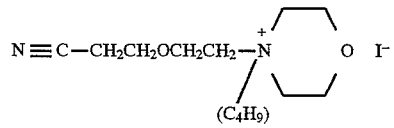

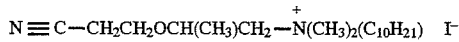

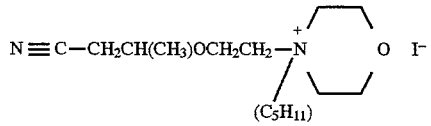

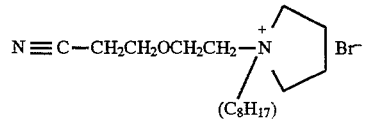

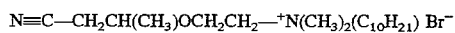

The catalyst "C" having formula (I) with "r" equal to 0 can be prepared preferably, but not exclusively, by a quaternization process of a tertiary amine, or mixtures of different tertiary amines, having formula (VI)

$NR_1R_2R_3$         (VI)

with a halo-nitrile, or mixture of different halonitriles, having formula (VII).

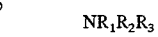         (VII)

In these formulas (VI) and (VII) Z, Y, $R_1$, $R_2$, $R_3$ and X have the same meanings defined above in the description of general formula (I) of the catalyst. According to this synthesis method, suitable amines having formula (VI) are selected from the group of tertiary amines which are aliphatic, cycloaliphatic, aromatic, heteroaromatic or with a mixed structure containing a total number of carbon atoms of between 3 and 24. Examples of these amines are: triethylamine, N,N-dimethyl-butylamine, N-methyl-dipropylamine, N,N-dimethyl-hexylamine, tripropylamine, N,N-dimethyl-octylmaine, tributylamine, N,N-dimethyl-dodecylamine, trihexylamine, trioctylamine, N-ethylmorpholine, N-ethylpiperidine, N-butylpyrrolidine, 4-ethylpyridine, 4-terbutylpyridine, N,N-diethylaniline, 4-(1-butyl-pentyl)pyridine, N-ethyl-bis(3-phenylpropyl) amine.

According to this synthesis method of catalyst "C" by the quaternization of tertiary amines of the types listed above, suitable halo-nitriles having general formula (VII) are preferably selected from the group of aliphatic ω-halo-nitriles having formula (VIII)

         (VIII)

with "p" greater than or equal to 1.

Suitable aliphatic ω-halo-nitriles of this type comprise 4-bromobutyrronitrile, 5-bromovaleronitrile, 6-bromocapronitrile, 7-bromoheptanonitrile, 8-bromocaprylonitrile, 4-iodobutyrronitrile, 5-iodovaleronitrile, 7-iodoheptanonitrile.

According to the above method for the preparation of the catalyst, the tertiary amine, or a mixture of tertiary amines, having formula (VII) and ω-halo-nitrile, or a mixture of different ω-halo-nitriles, having formula (VIII) are reacted with each other in such quantities that the molar ratio between the tertiary amino groups and alkyl halide is not more than 1, and preferably equal to 1. The reaction can be carried out using the normal known quaternization processes, and in particular alkylation, of tertiary amines.

The preparation can be carried out both without and, optionally, with the help of solvents which are inert or not very reactive with the chemical functionalities of the above reagents and, preferably, sufficiently volatile to be easily eliminated by distillation at the end of the reaction. For this purpose, it is possible to use the same solvents previously listed for possible use in the process for the preparation of the catalyst "C" according to the cyanoalkylation and quaternization method described above. Also in this case, the preparation is preferably carried out without solvents, or with as small a quantity as possible thereof.

For purely illustrative purposes which do not limit the scope of the present invention, the preparation is conveniently carried out by the gradual addition under stirring of the tertiary amine, or mixture of tertiary amines, to the ω-halo-nitrile or mixture of different ω-halo-nitriles (containing the optional solvent or mixture of solvents), maintaining the temperature at a value of between 0° and 50° C., and, at the end of the addition, heating the total mixture to a temperature of between 50° and 120° C., at which it is maintained, still under stirring, for a period varying from 4 to 40 hours.

The catalysts having formula (I) used in the compositions of the present invention can be either liquid or solid, but, in a particularly preferred form of embodiment, they are liquids more or less viscous at temperatures of less than 60° C., or even better, of less than 20° C.

Component "A", consisting of a polyepoxide, or a mixture of different polyepoxides or of one or more polyepoxides with one or more monoepoxides, is a liquid more or less viscous at temperatures lower than 160° C. In a preferred form of embodiment of the present invention, said component "A" is liquid at temperatures lower than 100° C., and even better at temperatures lower than 20 ° C.

Component "B", consisting of an anhydride, or a mixture of different anhydrides, of di- or poly-carboxylic acids, is liquid at temperatures lower than 160° C., and preferably at temperatures lower than 100° C.

The reactive compositions of the present invention are prepared by combining components "A" and "B" in such quantities that the ratio between the number of epoxide groups and the number of anhydride groups is between 0.9 and 1.3, and preferably between 0.95 and 1.2.

In their liquid state, "A" and "B" are completely and rapidly mixable with each other in the composition ratios "A"/"B" specified above, and preferably in all the "A"/"B" ratios. These mixtures "A"+"B" are liquid at temperatures lower than 100° C., and preferably at temperatures lower than 20° C.

The catalyst "C" is contained in the total reactive composition in a quantity of between 0.05 and 5 parts by weight per 100 parts by weight of mixture "A"+"B" of epoxides and anhydrides, and preferably in a quantity of between 0.1 and 1 parts by weight.

Said catalyst is soluble in the liquid mixtures of "A" and "B" in the ratios defined above. It is preferably soluble in the mixtures of "A" and "B" in all the ratios, in the liquid component "A" or in the liquid component "B" separately, and even more preferably in both.

Besides the above components "A", "B" and "C", the compositions of the present invention can contain, in addition, additives and auxiliaries, as well as their combinations, the use of which is well known to experts in the field of plastic materials and thermosetting resins. These products are generally added to obtain polymeric materials having suitable characteristics for different applications (for example, increasing the duration, giving flame-retardancy, improving the mechanical properties, etc.), to improve the processability, or simply to reduce the cost of the material itself.

Among the additives of the known art which can be advantageously used for the purposes of the present invention, either alone or combined with each other, are mineral fillers such as kaolin, talc, mica, calcium carbonate, dolomite, alumina, quartz or glass powder, titanium dioxide, various oxides, sulfides and chromates of heavy metals, carbon black, short or milled glass fibers, carbon fibers, asbestos fibers and other inorganic fibers; lubricating powders such as graphite powder and molyibdenum sulfide powder; flame-retardants both inorganic such as antimonium trioxide, metal borates and phosphates, and organic such as various polyhalogenated compounds, organic phosphates and phosphonates.

Other additives and auxiliaries which can be used either alone or together with those listed above or with each other, comprise antioxidants, dyes, diluents, release agents, thixotropic agents, foaming agents, and also antifoam agents, propellants, suspending agents, emulsifiers and others, whose use is known in the art.

As already mentioned, when the compositions of the present invention are used for the production of manufactured or semi-manufactured articles in reinforced composite materials, they can contain tough fibers, either continuous and/or chopped into various lengths, such as glass fibers, carbon fibers, boron fibers, silicon carbide fibers, ceramic fibers, metallic fibers, aramidic fibers or other known fibers and their combinations, arranged in various ways in tapes, ribbons, cords, fabrics, non-woven fabrics, mats and the like, possibly combined with other metallic or non-metallic structures or inserts. These tough fibers are conveniently added in a quantity of between 0 and 70% by weight with respect to the total weight of the composition.

The reactive compositions of the present invention are liquid at temperatures lower than 100° C., and preferably at temperatures lower than 20° C. These compositions are characterized by a prolonged pot-life, usually of between an hour and several tens of hours, at temperatures ranging from room temperature to 100° C., after which they still remain fluid and processable for a further period of time varying from several hours to a few days, depending on the type of components "A" and "B", the concentration of the catalyst and temperature.

At the same time, these compositions are surprisingly susceptible to rapid conversion into a solid polymeric material (in times varying typically from several minutes to a few hours at temperatures ranging from room temperature to 100° C.) by means of a polymerization process carried out under microwave irradiation, a process promoted by the catalyst "C". The times necessary for the gelation and subsequent solidification of the present compositions, within the ranges previously specified, decrease with an increase in the treatment temperature, the power of the microwave radiation and quantity of catalyst "C".

As already mentioned, the cross-linkable liquid compositions of the present invention can be advantageously and preferably polymerized by a process, whose form is also one of the objects of the present invention, comprising the following steps:

(i) mixing components "A", "B" and "C" and the possible additives until a homogeneous liquid mixture is obtained;

(ii) introducing or passing the mixture prepared in (i) into a microwave heating apparatus operating with an electromagnetic radiation having a frequency within the range of 0.5 GHz to 20 GHz;

(iii) subjecting the mixture introduced into the apparatus of (ii) to microwave radiation for a period of more than 1 minute at a temperature higher than 40° C., preferably between 60° and 120° C.

In step (iii) of the above process, the mixture is preferably subjected to radiation for a period of between 15 and 150 minutes.

For the preparation of the reactive compositions, in step (i) of the process of the present invention, any of the different methods suitable for the purpose and known in the field of thermosetting resins, can be used. The selection of the mixing method which is most convenient each time can be carried out by an expert in the field on the basis of the type of technology selected for the fabrication of the manufactured or semi-manufactured product to be obtained, as well as the production times desired or at least compatible with the gelation and solidification times of the composition itself.

In a typical but non-limiting example, step (i) can be conveniently carried out by mixing components "A", "B" and "C" and the other possible additives and auxiliaries, in suitable quantities, in a container with the help of a mixing/homogenization apparatus selected from the numerous ones available on the market of either industrial or laboratory type.

In another form of embodiment, components "A" and "C", or "B" and "C", can be premixed with each other in suitable quantities, in order to prepare a premixed component "A"+"C" or "B"+"C", which by mixing with "B" or "A" respectively, can complete the preparation of the compositions of the present invention before their use. The possible additives or auxiliaries can in turn be introduced after premixing with one of components "A" or "B", or with the respective premixtures "A"+"C" or "B"+"C". In this respect, the complete freedom offered by the catalyst "C" of the present invention in selecting the operating conditions for the preparation of these compositions, is particularly advantageous. In fact, catalysts "C", having the structure of formula (I), are rapidly and completely soluble both in component "A" and component "B", as well as in mixtures of the two. In addition, the excellent stability of each single component and of mixtures "A"+"C" or "B"+"C", which are capable of maintaining their original rheological characteristics for very long times, as long as several months, at temperatures of up to 70° C., as well as the prolonged times of use (several hours) of the whole compositions at the same temperatures, allow not only the single components but also their mixtures to be suitably heated in order to reduce their viscosity and make all the dosing, mixing, degassing operations under vacuum and all the other necessary procedures more rapid and efficient. The possibility of using the compositions of the present invention for a very extensive period of time even under heat together with the surprising rapidity of their polymerization under the effect of microwaves, enormously satisfies the requisites of a wide variety of processing technologies and guarantees great versatility of the present invention, especially in cases where considerable quantities of solid, particulate additives, such as, as mentioned above, mineral fillers, fibers or pigments, are introduced into the mixture.

According to another example for the embodiment of the present invention, step (i) for the preparation of the above cross-linkable liquid compositions can be carried out, with well-known methods, by the simultaneous and continuous mixing of components "A" and "B" and the catalyst "C". These, in other words, are forced to flow, in the suitable quantitative ratios, and are conveyed and mixed in extremely rapid times, through a pipe, cavity, nozzle or similar geometrically suitable element, with the formation of the homogeneous liquid composition, which is then fed directly to the device through which it is injected, sucked, cast or spread. In a variation of this latter method, the compositions of the present invention can be prepared with the same equipment, but premixing, in suitable containers connected to the feeding lines, the catalyst "C" with component "A" or "B" respectively, or premixing components "A" and "B". The various optional additives and auxiliaries are preferably premixed and homogeneously dispersed with one or both of components "A" or "B" or with one of the mixtures "A"+"B", "A"+"C" or "B"+"C".

In step (ii) of the process of the present invention, the composition prepared in step (i) is transferred or passed, either in continuous or batch, into a microwave device having the shape and characteristics suitably selected on the basis of the transformation technology used and the shape and dimensions of the manufactured or semi-manufactured products required.

According to step (iii) of the present process, the cross-linkable compositions of the present invention are hardened by subjecting them to radiation by source of electromagnetic energy with frequencies in the range of microwaves. For this purpose, any apparatus can be used comprising a device for the emission of microwaves connected to a suitable chamber or pipe forming a resonat cavity or waveguide. Numerous examples of these devices, not limited to the present invention, are provided in the publication "Industrial Microwave Heating" by the authors A. C. Metaxas and R. J. Meredith, published by Peter Peregrinus Ltd., London (1983), whose contents should be considered as being an integrant part of the present invention.

A preferred apparatus for carrying out step (iii) of the present process comprises a single-mode resonat cavity. The present invention, however, should not be limited to this apparatus but can also be satisfactorily carried out with other microwave treatment devices.

The application of the electromagnetic radiation in step (iii) of the present process can be either continous or pulsed. In the first case the hardening times are shorter, but it becomes more difficult to control the temperature profile during polymerization, with possible local overheating. In some cases it may be convenient to use an electromagnetic radiation with modulated power.

In the process of the present invention, step (iii) can be conveniently carried out by applying pulsed radiation. This can be easily achieved using an oscillator inserted in the microwave circuit before the resonat cavity. The use of pulsed electromagnetic radiation permits excellent temperature control and, when required, allows the polymerization process of the compositions to be carried out isothermally.

The polymerization process with microwaves of the compositions of the present invention can be conveniently carried out using any of the methods and equipment of the known art suitable for the purpose. A wide variety of microwave generators is available on the market on an industrial or laboratory scale, which can operate with a fixed frequency (typically 915 MHz and 2.45 GHz), or with frequencies varying within a wide range, typically between 0.5 and 20 GHz. These generators provide an operating power which varies from several tens of Watts, up to 10 kW and over. Also the oscillators used for obtaining pulsed electromagnetic radiation are well known to experts in microwave technology. Examples of schematic representations of equipment for microwave treatment on a laboratory scale, suitable for the embodiment of the process of the present invention, are provided by J. Jow et al. in the publication "SAMPE Quarterly", January 1989, page 46, the contents of which should be considered as forming an integrant part of the present application as reference.

In the process of the present invention, the selection of the microwave irradiation power can be easily made by those skilled in the art on the basis of the technologies used, dimensions of the molded articles, characteristics of the cross-linkable composition, etc.

According to a preferred form of embodiment, the polymerization process of the present invention is carried out by placing the reactive composition, typically casted or poured into a suitably shaped mold, into the resonat cavity connected to the microwave generator and possible oscillator. The composition is then subjected to either continuous or, preferably, pulsed radiation, until the desired polymerization degree is reached or until the end of the chemical process. The optimum period and intensity of the radiation are experimentally set for each single application of the process according to the normal optimization methods available to experts in the field. The heating control of the mixture is generally achieved by means of a suitable temperature detection probe. At the end of the treatment, the polymerized composition is removed from the cavity and, possibly, checked.

In another variation of the process of the present invention, steps (i), (ii) and (iii) previously described can also be carried out in succession in a single container or duct, suitably shaped and arranged.

In a particular form of embodiment of the present invention, the process for solidifying the reactive compositions previously described also comprises, during step (iii), in addition to the microwave radiation and simultaneously or subsequent thereto, the application of thermal heating by exposure of these compositions to a conventional source of heat. This additional thermal treatment is preferably carried out at temperatures of between 60° and 120° C. and for a period of between 15 and 150 minutes.

According to a preferred form of embodiment of the present invention, the solid polymeric material resulting from the rapid polymerization step (iii) under the action of microwaves alone, or these combined with possible thermal treatment, is usually subjected to subsequent post-polymerization treatment at a higher temperature to complete the polymerization reactions.

This post-polymerization treatment of the already solidified composition can be carried out by maintaining it at a temperature within the range of between 80° and 250° C., and, preferably, between 100° and 200° C., for a period of between 0.5 and 24 hours, preferably between 1 and 12 hours. According to the present invention, the post-polymerization treatment can also be advantageously carried out by microwave radiation or by the combined action of microwaves and thermal heating, using equipment and procedures which are basically analogous to those previously described for the solidification step. The post-polymerization process does not necessarily require the removal of the molded article from the resonat cavity, but can be conveniently carried out therein by simply continuing the radiation and/or heating beyond the hardening step, under progressively more intense conditions.

The present invention also relates however to possible post-polymerization treatment carried out by heating with only traditional thermal sources such as resistances, air or other hot gas heating, infrared sources, etc.

The cross-linkable liquid compositions of the present invention, by suitable polymerization and post-polymerization treatment according to one of the methods already mentioned, preferably carried out with microwaves, allow the production of molded, manufactured or semi-manufactured products, consisting of a hard or tough polymeric material, preferably having a softening temperature of between 100° and 200° C., a high elastic modulus value, good dielectric rigidity, good resistance to solvents and excellent radiation resistance to prolonged exposure to sun light and artificial UV radiations, as well as high adhesion to many substrates such as metals, glasses and ceramic materials.

In accordance with this, the reactive compositions of the present invention are particularly suitable, independently of the presence or not of additives, auxiliaries or reinforcing fibers, for the rapid production of manufactured or semi-manufactured devices or articles, such as electrical components and encapsulated electrical/electronic devices, and also as adhesives, seals, linings, coatings, etc., for out-door applications, i.e. involving prolonged exposure to sun light.

For this purpose, for example, a portion of a cross-linkable liquid composition of the present invention, brought to a temperature which is sufficient to give it the necessary fluidity, can be:

a. cast, injected or sucked into open or closed molds, for the manufacture of various articles such as electric insulators, connectors, switches, relais, etc.;

b. fed by rigid or flexible pipes to containers for the embedding, encapsulation or filling of internal cavities, operating under vacuum or under pressure or with a combined vacuum and pressure action, electrical or electronic devices or their preformed assembly;

c. poured into containers in which parts of electrical or mechanical equipment are dipped and removed once or several times to obtain insulating or protective coatings or linings.

Once the filling of the mold, container or cavity has been completed, or the coating of the surfaces of the device to be treated, and after carrying out the possible degassing, the reactive composition is rapidly and uniformly polymerized by microwave irradiation. The hardening process can then be completed by continuing the irradiation or by subjecting the article or device to a separate post-polymerization treatment according to what is specified above.

The compositions of the present invention are also particularly suitable for the rapid and continuous production of manufactured or semi-manufactured elements such as bars, beams, profiles, pipes or slabs in structural composite material by means of the known "pultrusion" or "pulforming" methods, preferably modified in line for the application of the microwave polymerization process. For this purpose, the reactive composition in the liquid state is co-extruded in continuous, together with tapes, ribbons, cords, mats, fabrics, non-woven fabrics and similar versions of glass, carbon, polyaramide (Kevlar®), etc. reinforcing fibers, as well as metal wires or tapes, which are thus continuously impregnated and embedded in the same liquid composition. The composition, prepared apart prior to extrusion, is charged into a suitable container from which it is continuously pumped and sent to the impregnation zone of the equipment, located before the extrusion head.

According to the present invention, the systems consisting of the reactive composition embedding the fibrous structures and the other possible constituents is then rapidly solidified by passing it continuously (for example by conveyor belts) into a suitable apparatus for microwave irradiation, such as, for example, a tunnel or tubular microwave oven, a microwave wave guide or similar device, possibly combined with or co-assembled with a device for thermal heating, situated immediately after the extrusion die.

In conformity with what has generally been previously observed for microwave treatment, even when the present process and present cross-linkable compositions are used in "pultrusion" or "pulforming" technologies, it is preferable for the solidification step to be followed by a post-polymerization step, which can be carried out by microwave heating or in a thermal oven or by a combination of the two systems, although partial or total use of microwaves guarantees a better quality of the articles obtained at the end and is therefore preferred. Also in this case, the post-polymerization treatment can be conveniently carried out in continuous at the tail or by an extension of the production line described above.

The compositions and process of the present invention can also be effectively used for the rapid coating of surfaces of various articles and devices to protect and insulate them (electrically), and also for the rapid and long-lasting sealing and repairing of parts of various items and articles, or for the welding of joints between different elements. In this case, the composition of the present invention can be prepared in separate portions, or also by the continuous mixing of the components, and subsequently spread onto the surfaces or injected into the joints to be subjected to gluing treatment, and then rapidly polymerized by microwave irradiation. One of the advantages of the present invention lies particularly but not exclusively in this latter case, in the fact that microwave irradiation is capable of causing the solidification of the compositions without any need for heating the entire mass of the object to be coated, glued or repaired, with obvious time and energy saving and the possibility of subjecting to treatment objects containing parts which are sensitive to heat but not susceptible to heating under microwaves.

When used for coating, the cross-linkable compositions of the present invention can comprise, in addition, solvents and diluents suitable for reducing their viscosity and improving their spreadability. These can be then removed by evaporation at suitable temperatures, before the solidification step.

The present invention is illustrated in detail by the following examples, which however are purely indicative and do not limit the scope of the invention itself.

EXAMPLES

In the following examples, all the microwave polymerization experiments were carried out using equipment supplied by the Company Wavemat, Inc. (Plymouth, Mich., U.S.A.), characterized by a single-mode resonat cavity of about 18 cm in diameter. The equipment basically consists of an electromagnetic radiation generator with varying power operating at a frequency of 2.45 GHz and capable of supplying a maximum power of 40 Watt, and a unit for programming the temperature control. With this device it is possible to carry out the polymerization of the compositions of the present invention both with a constant irradiation power, by recording the temperature in relation to the time, and isothermally by the pulsed emission of microwaves controlled by a sequential feed-back system. When necessary, the temperature is controlled by using a Luxtron 755 fluoroptic apparatus. The cross-linkable compositions to be irradiated during the polymerization cycle are conveniently placed in Teflon vessels to minimize the amount of energy absorbed by the vessel itself and improve the precision of data provided by the control and recording equipment.

At the beginning of the polymerization, the probe for measuring the temperature is immersed in the liquid mass of the cross-linkable composition where it remains subsequently embedded when the polymerization has been completed. In this way the temperature of the sample is measured with great precision in relation to the time.

In the following examples, the viscosity of some of the components of the reactive compositions was measured by a Brookfield viscometer (Brookfield viscosity).

The glass transition temperature (Tg) of the compositions after polymerization was determined by measurements of the dielectric constant and dissipation factor in relation to the temperature, by dielectric thermal analysis at a frequency of 1 kHz and with a scanning rate of 2° C./minute, carried out with a DETA analyzer, Polymer Laboratories Ltd. With this analysis technique, the Tg is defined as the temperature at which a peak appears on the dissipation factor diagram in relation to the temperature of the sample. When it was not possible to determine this peak temperature with sufficient precision, an operating definition of the Tg was used, identified as the temperature at which the start of a rapid increase in the dissipation factor is observed.

EXAMPLE 1

A solution of 26.49 grams of N-(2-hydroxyethyl) morpholine and 0.15 grams of benzyltrimethylammonium hydroxide 40% by weight in methanol was placed in a three-necked 100 ml flask, equipped with a reflux condenser, thermometer and dropping funnel. 13.55 grams of freshly distilled crotononitrile were slowly added dropwise in a 15÷20 minute period to this solution, cooled to 0° C. with an ice bath and maintained under magnetic stirring. During the addition, the temperature was maintained at 20°÷25° C. still under cooling with an ice bath. The mixture was then left under stirring for an hour at room temperature and subsequently heated in a silicon oil bath to 70° C. for further six hours. After cooling to room temperature, 40.00 grams of 1-iodopentane were added dropwise under stirring. The mixture was then heated to 80° C. and maintained at this temperature for 14 hours, during which a gradual increase in the viscosity was observed.

The catalyst thus prepared is, at room temperature, an amber-colored liquid having a honey-like consistency.

A liquid reactive composition was prepared by mixing at 45° C. the following products:

23.60 grams of a cycloaliphatic epoxy resin consisting of 3,4-epoxycyclohexylmethyl-3',4'-epoxycyclohexanoate, having an epoxy equivalent weight of 132.6 and a Brookfield viscosity at 25° C. of 394 cPs;
  27.10 grams of hexahydrophthalic anhydride;
  0.23 grams of the catalyst described above.

A portion of 3 grams of this composition was placed in a small cylindrical Teflon vessel and the temperature probe, protected by a glass sheath, was placed in the center of the sample of liquid reactive mixture. The sample was rapidly placed in the Wavemat microwave resonat cavity.

An isothermal polymerization experiment under pulsed microwave irradiation was carried out bringing the mixture to a nominal temperature of 85° C. and maintaining it as such for 60 minutes. During this period of 60 minutes, the temperature oscillated between 84° and 87° C., indicating the good isothermal control of the system during the polymerization reaction.

At the end of the experiment, a small cylinder of solid polymeric material was removed from the microwave apparatus, and the glass transition temperature was determined by dielectric thermal analysis. Using a frequency of 1 kHz and a heating rate of 2° C./min a Tg value of about 60° C. was determined. The polymeric material was subsequently subjected to post-polymerization in a conventional hot-air oven for 2 hours at 120° C. and 1 hour at 150° C., obtaining a material with a glass transition temperature of about 155° C.

For comparative purposes, 3 grams of the same composition were placed in a conventional hot-air oven at the same constant temperature of 85° C. used for the microwave isothermal polymerization. Contrary to what was observed in the microwave treatment, after a period of 150 minutes, the mixture was still liquid and very fluid. Gelation did not occur before about 270 minutes, and a solid polymeric material was only obtained after about 450 minutes.

To evaluate the efficiency of the specific catalyst described above, a further comparative isothermal polymerization experiment was carried out under pulsed microwave irradiation at the same temperature of 85° C., using the same epoxy/anhydride mixture as above, but using, instead of the specific catalyst, a conventional catalyst of a similar type in an equal molar concentration. For this purpose, a reactive composition was prepared consisting of:

4.59 grams of the same cycloaliphatic epoxy resin mentioned above;

5.35 grams of hexahydrophthalic anhydride;

0.056 grams of tetrabutylammonium iodide.

An aliquot of 3 grams of this composition was subjected to microwave isothermal treatment at 85° C. Contrary to the first experiment described in the present example, the product was still liquid after 60 minutes. A further 60 minutes of microwave irradiation produced a gelled but still not solidified material.

EXAMPLE 2

A liquid catalyst was prepared following the same procedure described in Example 1, but using the following reagents: 14.58 g of 3-dimethylamino-2-propanol, 0.066 g of tetramethylammonium hydroxide pentahydrate, 7.50 g of acrylonitrile and 37.90 g of 1-iododecane. At the end of the preparation, a catalyst was obtained having, at room temperature, the appearance of a yellowish viscous liquid.

A liquid reactive composition was prepared by mixing at 50° C.:

21.00 grams of a cycloaliphatic epoxy resin consisting of 2-(3,4-epoxycyclohexyl-5,5-spiro-3',4'-epoxycyclohexane)-methadioxane, having an epoxy equivalent weight of 148 and a Brookfield viscosity of 11500 cPs at 25° C.;

39.00 grams of 2-dodecen-1-ylsuccinic anhydride;

0.28 grams of the catalyst described above.

A portion of 10 grams of this composition was transferred to a small cylindrical Teflon vessel, and the probe for the temperature control was positioned in the center of the sample. The vessel was then placed in the Wavemat microwave resonat cavity. An isothermal polymerization experiment at 70° C. with pulsed irradiation was then initiated. With a treatment of 3 hours at this temperature, the product was converted to a rubbery gelled material. A further 3 hours at 70° C. brought the material to a glass state with a Tg value of 73° C. The post-polymerization of this product for 2 hours at 130° C. and 2 hours at 160° C. in a conventional hot-air oven produced a final material having a Tg of 172° C.

For comparative purposes, a second portion of 10 grams of liquid reactive composition was placed in a conventional hot-air oven regulated at a constant temperature of 70° C. Under these treatment conditions, gelation of the product took place only after about 25.5 hours, and the formation of a glass material did not occur until after 63 total hours from the beginning of the experiment.

EXAMPLE 3

A liquid catalyst was prepared following the same procedure described in Example 1 using the following reagents: 17.01 g of 3-dimethylamino-1-propanol, 0.42 g of benzyltrimethylammonium hydroxide 40% by weight in methanol, 8.75 g of acrylonitrile and 44.2 g of 1-iododecane. With respect to Example 1, in this preparation the cyanoalkylation step at 70° C. lasted 2 hours, whereas the quaternization with iododecane was carried out in 12 hours at 70° C.

A liquid reactive composition was prepared by mixing at room temperature:

31.4 grams of an epoxy resin consisting of polypropylene glycol diglycidylether, having an epoxy equivalent weight of 318 and a Brookfield viscosity of 70 cPs at 25° C.;

16.5 grams of methyl-hexahydrophthalic anhydride;

0.29 grams of the catalyst prepared as described above.

Two 3 gram portions of this composition were subjected in Teflon vessels to two cycles of isothermal polymerization treatment under pulse microwave irradiation using the same procedure as Examples 1 and 2 at the two different temperatures of 80° and 105° C. for 60 minutes and, respectively, 45 minutes. During the two experiments, at the end of which a tough solid elastomeric material was obtained, the temperature recordings of the samples showed values varying within the range 79°÷82° C. and, respectively, 105°÷111° C., demonstrating in both cases good isothermal control of the system during the polymerization reaction. At the end of the two experiments, a determination was carried out by means of DETA of the Tg of the materials at a frequency of 1 kHz and at a scanning rate of 2° C./min, obtaining in both cases a value of about −45° C.

For comparative purposes, two aliquots of 3 grams each of the same reactive composition were subjected to two cycles of conventional thermal treatment in a hot-air oven at the two temperatures of 80° and 105° C. Contrary to the results of the corresponding microwave treatment, after 150 minutes at 80° C. and after 75 minutes at 105° C., the composition was still liquid and very fluid, indicating an extremely reduced polymerization degree.

EXAMPLE 4

A liquid catalyst was prepared basically following the same procedure described in Example 1 using the following reagents: 11.80 g of 2-dimethylamino-1-ethanol, 0.31 g of benzyltrimethylammonium hydroxide 40% by weight in methanol, 8.88 g of crotononitrile and 29.28 g of 1-bromodecane. With respect to Example 1, the quaternization with bromodecane was carried out in 6 hours at 70° C. followed by 12 hours at 85° C. The catalyst obtained is, at room temperature, a very viscous brown liquid.

A liquid reactive composition was prepared by mixing at room temperature:

7.58 grams of 1,2,5,6-diepoxycyclo-octane;

17.40 grams of a liquid mixture, previously prepared at 45° C., consisting of 70% by weight of hexahydrophthalic anhydride and 30% by weight of methylhexahydrophthalic anhydride;

0.15 grams of the catalyst prepared as described above.

A portion of 10 grams of this composition was transferred to a small cylindrical Teflon vessel, and the probe for the temperature control was positioned in the center of the sample. The vessel was then placed in the Wavemat microwave resonat cavity. An isothermal polymerization experiment at 100° C. under pulsed irradiation was then started. After a treatment of 50 minutes at this temperature, the gelation of the composition was reached. A further 20 minute treatment at 100° C. (70 minutes from the beginning of the experiment) brought the material to a glassy state. The small cylinder of the material thus obtained was subjected to a cycle of isothermal post-polymerization at 150° C. for 1 hour under pulsed microwave irradiation in the same Wavemat cavity. At the end of the treatment a material was obtained having a Tg of 130° C., according to the DETA determination already described.

For comparative purposes, a second portion of 10 grams of the liquid reactive composition was placed in a conventional hot-air oven regulated at a constant temperature of 100° C. Under these treatment conditions, gelation of the product took place only after about 105 minutes, and the formation of a glass material did not occur until after 160 minutes from the beginning of the experiment.

EXAMPLE 5

In a three-necked 100 ml flask, equipped with a reflux condenser, thermometer and dropping funnel, 24.94 grams of 4-bromobutyronitrile were placed and then 27.10 grams of N,N-dimethyl-octylamine were slowly added dropwise in 15÷20 minutes under vigorous magnetic stirring. During the addition, the temperature was maintained at 20°÷25° C. by external cooling in an ice bath.

The mixture was then maintained, under stirring, for 15 minutes at room temperature and subsequently brought to 95° C. and maintained at this temperature for 30 hours.

At room temperature the catalyst thus obtained is a yellow-orange colored liquid with a honey-like consistency.

A liquid reactive composition was prepared by mixing at room temperature the following products:

26.76 grams of a cycloaliphatic epoxy resin consisting of 3,4-epoxycyclohexylmethyl-3',4'-epoxycyclohexanoate, having an epoxy equivalent weight of 132.6 and a Brookfield viscosity of 394 cPs at 25° C.;

33.24 grams of methyl-hexahydrophthalic anhydride;

0.24 grams of the catalyst described above.

A 5 gram portion of this composition was transferred to a small cylindrical Teflon container, and the probe for the temperature control was positioned at the center of the sample. The vessel was then placed in the Wavemat microwave resonat cavity.

An isothermal polymerization experiment under pulsed microwave irradiation was carried out bringing the mixture to 95° C. and maintaining it at this temperature for 40 minutes. In this period of time the reactive composition was converted to a glassy polymeric material.

For comparative purposes, 5 grams of the same composition were placed in a conventional hot-air oven at the same constant temperature of 95° C. used for the isothermal microwave polymerization. Contrary to what was observed in the microwave treatment, gelation did not occur before 130 minutes, and a glassy material was not obtained until after 250 minutes from the beginning of the experiment.

EXAMPLE 6

A liquid catalyst was prepared following the same procedure described in Example 1, using the following reagents: 17.67 g of N-(2-hydroxyethyl)morpholine, 0.094 g of benzyltrimethylanunonium hydroxide 40% by weight in methanol, 7.15 g of acrylonitrile and 24.80 g of 1-iodobutane. At the end a catalyst was obtained having, at room temperature, the appearance of a brown viscois liquid.

A liquid reactive composition was prepared by mixing at 40° C. the following products:

23.80 grams of a cycloaliphatic epoxy resin consisting of bis(3,4-epoxycyclohexylmethyl)-adipate, having an epoxy equivalent weight of 196.5 and a Brookfield viscosity at 25° C. of 630 cPs;

8.10 grams of methyl-hexahydrophthalic anhydride;

8.10 grams of succinic anhydride;

0.16 grams of the catalyst described above.

A 10 gram portion of this composition was placed in a small cylindrical Teflon vessel and the probe for the temperature control was positioned in the center of the sample of liquid reactive mixture. The sample was rapidly placed in the Wavemat microwave resonat cavity.

An isothermal polymerization experiment under pulsed microwave irradiation was carried out bringing the mixture to 90° C. and maintaining it at this temperature. Gelation of the composition occurred within a period of 50 minutes, whereas the vitrification of the material was obtained after 110 minutes from the beginning of the experiment. The polymeric material itself was subsequently subjected to isothermal post-polymerization for 1 hour at 180° C. under pulsed microwave irradiation, obtaining a material with a glass transition temperature of about 125° C. determined by DETA.

For comparative purposes, 10 grams of the same composition were placed in a conventional hot-air oven at the same constant temperature of 90° C. used for the isothermal microwave polymerization. Contrary to what was observed in the microwave treatment, gelation and vitrification of the product took place after 7 and, respectively, 14.5 hours from the beginning of the thermal treatment.

EXAMPLE 7

A liquid catalyst was prepared following the same procedure described in Example 1, using the following reagents: 11.33 g of N-(2-hydroxyethyl) morpholine, 0.094 g of benzyltrimethylammonium hydroxide 40% by weight in methanol, 5.79 g of crotononitrile and 34.9 g of 1-iodo-octadecane. With respect to Example 1, the quaternization with iodo-octadecane was carried out in 18 hours at 80° C. followed by 12 hours at 90° C. The catalyst obtained is, at room temperature, a reddish-colored transparent product with a doughy consistency.

A liquid reactive composition was prepared by mixing at 50° C. the following products:

10.65 grams of 1,2,7,8-diepoxyoctane 39.35 grams of 2-dodecen-1-ylsuccinic anhydride;

0.37 grams of the catalyst described above.

A 20 gram portion of this composition was placed in a small cylindrical Teflon vessel and the probe for the temperature control was positioned in the center of the sample. The sample was rapidly placed in the Wavemat microwave resonat cavity.

An isothermal polymerization experiment under pulsed microwave irradiation was carried out bringing the mixture to a nominal temperature of 60° C. and maintaining it at this temperature. During the experiment the temperature oscillated between 58.4 and 60.7° C., indicating a good isothermal control of the system during the polymerization process. After a treatment of 2 hours gelation of the composition was reached, whereas a further 2.5 hours of treatment (total 4.5 hours from the beginning of the experiment) brought the material to its glassy state. The polymeric material itself was subsequently subjected to post-polymerization in a conventional hot-air oven for 4 hours at 150° C., obtaining a material with a glass transition temperature of about 128° C.

For comparative purposes, 20 grams of the same composition were placed in a conventional hot-air oven at the same constant temperature of 60° C. used for the isothermal microwave polymerization. With respect to what was observed in the microwave treatment, gelation and vitrification of the product took place after 18 and, respectively, 34 hours from the beginning of the thermal treatment.

EXAMPLE 8

A liquid catalyst was prepared following the same procedure described in Example 5, but using the following reagents: 19.04 g of N,N-dimethyl-octylamine and 23.05 g of 7-bromoheptanonitrile. The catalyst obtained is, at room temperature, a very viscous brown liquid.

A liquid reactive composition was prepared by mixing at room temperature:

9.06 grams of 1,2,5,6-diepoxycyclo-octane;

20.94 grams of a liquid mixture, previously prepared at 45° C., consisting of 50% by weight of hexahydrophthalic anhydride and 50% by weight of methylhexahydrophthalic anhydride;

0.17 grams of the catalyst prepared as described above.

A 10 gram portion of this composition was transferred to a small cylindrical Teflon vessel and the probe for the temperature control was positioned in the center of the sample. The vessel was then placed in the Wavemat microwave resonat cavity. An isothermal polymerization experiment at 105° C. with pulsed microwave irradiation was then carried out. After a treatment of 45 minutes at this temperature, gelation of the composition was reached. After 60 minutes of treatment from the beginning of the experiment the material reached its glassy state.

The small cylinder of the material thus obtained was subjected to a cycle of isothermal post-polymerization at 125° C. for 4 hours in a conventional hot-air oven. At the end of the treatment a material was obtained having a Tg of about 135° C., according to the DETA determination already described.

For comparative purposes, a second 10 gram portion of the liquid reactive composition was placed in a conventional hot-air oven regulated at the same constant temperature of 105° C. Under these treatment conditions, gelation of the product occurred after about 115 minutes, whereas the formation of glassy material took place after 180 minutes from the beginning of the experiment.

We claim:

1. Liquid reactive thermosetting compositions comprising:
   A) at least one polyepoxide or a mixture of one or more polyepoxides with at least one mono-epoxide, of aliphatic, cycloaliphatic or a mixture of these moieties;
   B) at least one anhydride of a di- or polycarboxylic acid of aliphatic, cycloaliphatic or a mixture of these moieties;
   C) at least one catalyst capable of promoting the rapid polymerization of the mixtures A+B under microwave irradiation and having general formula (I):

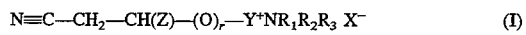

$$N\equiv C-CH_2-CH(Z)-(O)_r-Y^+NR_1R_2R_3\ X^- \qquad (I)$$

wherein r is 0 or 1;

Z is a hydrogen atom, or an aliphatic, cycloaliphatic, aromatic or heterocyclic radical, containing between 1 and 10 carbon atoms;

$R_1$, $R_2$, $R_3$, each the same or different, are aliphatic, cycloaliphatic, aromatic or heterocyclic radicals; jointly, $R_1$, $R_2$ and $R_3$ contain between 3 and 24 carbon atoms;

Y is an organic radical, containing between 1 and 16 carbon atoms, of aliphatic, cycloaliphatic, aromatic heterocyclic or a mixture of these moieties;

$X^-$ is a halide ion selected from chloride, bromide or iodide.

2. Compositions according to claim 1, wherein the average number of epoxy groups per molecule in component "A" is between 1.5 and 4.

3. Compositions according to claims 1 or 2, wherein Y, in formula (I) comprises heterocyclic, mixed aliphatic-heterocyclic, mixed cycloaliphatic-heterocyclic or heteroaromatic moieties or is also heterocyclic moiety with fused rings comprising the quaternary nitrogen atom, optionally comprising other heteroatoms apart from the quaternary nitrogen atom as part of the heterocyclic structure, and comprising one of the $R_1$ or $R_2$ radicals or both as part of the heterocyclic structure.

4. Compositions according to claim 3, wherein the quaternary nitrogen atom in formula (I) is part of a cycloaliphatic structure with fused rings wherein said quaternary nitrogen atom is part of two rings and comprising $R_1$ and $R_2$ as part of the heterocyclic structure.

5. Compositions according to claims 1 or 2, wherein the ratio between the number of epoxy groups and the number of anhydride groups is between 0.9 and 1.3.

6. Compositions according to claims 1 or 2, wherein the catalyst "C" is present in the entire reactive composition in an amount of between 0.05 and 5 parts by weight per 100 parts of mixture "A"+"B".

7. Process for the polymerization of the compositions according to claim 1, which comprises:
   (i) mixing components "A", "B" and "C" and optionally conventional additives until a homogeneous liquid mixture is obtained;
   (ii) introducing or passing the mixture prepared in (i) into a microwave heating apparatus operating with an electromagnetic irradiation having a frequency within the range of 0.5 GHz to 20 GHz;
   (iii) subjecting the mixture introduced into the apparatus of (ii) to microwave irradiation for a period of more than 1 minute at a temperature higher than 40° C.

8. Process according to claim 7, wherein in step (iii) the mixture is subjected to irradiation for a period of between 15 and 150 minutes and to a temperature of between 60° and 120° C.

9. Process according to claims 7 or 8, wherein the reactive composition is irradiated continuously or with pulses, until the desired polymerization degree is reached or until complete cure.

10. Process according to claims 7 or 8, wherein during step (iii), in addition to the microwave irradiation, thermal heating is applied, simultaneously or subsequently, by means of a conventional heat source.

11. Process according to claim 10, wherein said additional thermal treatment is carried out at temperatures of between 60° and 120° C. and for a period of between 15 and 150 minutes.

12. Process according to claims 7 or 8, wherein the solid polymeric material resulting from step (iii) is subjected to subsequent post-polymerization treatment at a temperature within the range of 80° to 250° C. and for a period of between 0.5 and 24 hours.

13. Process according to claim 12, wherein the post-polymerization treatment is carried out by microwave irradiation, or by the combined action of microwaves and thermal heating.

14. A method for the preparation of manufactured/semi-manufactured products, adhesives, seals, linings or coatings, comprising the process of claim 7.

15. Molded articles obtained by the process according to claims 7 or 8, having a softening point of between 100° and 200° C.

16. Articles according to claim 15, in the form of bars, beams, profiles, pipes or slabs, obtained by "pultrusion" or "pulforming" technologies.

* * * * *

UNITED STATES PATENT AND TRADEMARK OFFICE
CERTIFICATE OF CORRECTION

PATENT NO. : 5,650,477
DATED : July 22, 1997
INVENTOR(S) : Fabrizio PARODI et al.

It is certified that error appears in the above-indentified patent and that said Letters Patent is hereby corrected as shown below:

On the title page, Item [75], the 3rd inventor's address should read:

-- Hockessin, DE--

Signed and Sealed this

Second Day of December, 1997

Attest:

BRUCE LEHMAN

*Attesting Officer*      *Commissioner of Patents and Trademarks*